US012685877B1

(12) United States Patent
Tabibian

(10) Patent No.: US 12,685,877 B1
(45) Date of Patent: Jul. 21, 2026

(54) HANDHELD QUAD-MODAL SCALP TREATMENT DEVICE FOR ENHANCED HAIR LOSS THERAPEUTICS

(71) Applicant: Michael P. Tabibian, Los Angeles, CA (US)

(72) Inventor: Michael P. Tabibian, Los Angeles, CA (US)

(73) Assignee: ELLIYORA, INC., Wilmington, DE (US)

( * ) Notice: Subject to any disclaimer, the term of this patent is extended or adjusted under 35 U.S.C. 154(b) by 0 days.

(21) Appl. No.: 19/308,258

(22) Filed: Aug. 24, 2025

Related U.S. Application Data

(60) Provisional application No. 63/786,563, filed on Apr. 10, 2025.

(51) Int. Cl.
| | |
|---|---|
| *A61N 5/06* | (2006.01) |
| *A61B 5/00* | (2006.01) |
| *A61N 1/40* | (2006.01) |

(52) U.S. Cl.
CPC .......... *A61N 5/0617* (2013.01); *A61B 5/0077* (2013.01); *A61B 5/446* (2013.01); (Continued)

(58) Field of Classification Search
None
See application file for complete search history.

(56) References Cited

U.S. PATENT DOCUMENTS

| | | |
|---|---|---|
| 10,593,423 B2 | 3/2020 | Baldwin |
| 2004/0010418 A1 | 1/2004 | Buonocore et al. |

(Continued)

FOREIGN PATENT DOCUMENTS

| | | |
|---|---|---|
| CN | 107340865 B | 12/2020 |
| CN | 114587574 A | 6/2022 |

(Continued)

OTHER PUBLICATIONS

Marco Ruggiero, Chanting of Nam-Myoho-Renge-Kyo in the Context of the Buddhist Liturgy of Nichiren Shoshu: Study of Sound Frequencies, Brain Activity, and Microbial Metabolism, 14 pages, Preprints.org, Aug. 7, 2024, <https://www.preprints.org/manuscript/202407.0236>.

(Continued)

*Primary Examiner* — Mallika D Fairchild
(74) *Attorney, Agent, or Firm* — Vedder Price P.C.

(57) ABSTRACT

A handheld device for enhancing the topical absorption and efficacy of hair loss treatment compounds with integrated scalp analysis capabilities with a synchronized pulsed electromagnetic field (PEMF) generator; a dual-wavelength LED array; a zoned heating element; an ultrasonic molecular activation system operating at 20-35 kHz, a camera system with calibration targets; an adaptive protocol engine configured to receive real-time data from said integrated camera system, and in response, synchronously adjust at least one parameter of said PEMF generator, LED array, heating element, and ultrasonic system to optimize the delivery and efficacy of said hair loss treatment compounds; and a safety and control system including real-time scalp monitoring, follicular protection mechanisms, and acoustic exposure monitoring.

18 Claims, 5 Drawing Sheets

(52) U.S. Cl.
CPC .............. *A61B 5/4848* (2013.01); *A61N 1/40*
(2013.01); *A61B 2562/0271* (2013.01); *A61N*
*2005/0627* (2013.01); *A61N 2005/0644*
(2013.01)

(56) References Cited

U.S. PATENT DOCUMENTS

| | | | |
|---|---|---|---|
| 2004/0059220 | A1 | 3/2004 | Mourad et al. |
| 2005/0154382 | A1* | 7/2005 | Altshuler ............. A61B 18/203 |
| | | | 606/9 |
| 2008/0139974 | A1 | 6/2008 | Da Silva |
| 2011/0040235 | A1 | 2/2011 | Castel |
| 2013/0035539 | A1* | 2/2013 | Kornstein ................ A61N 1/40 |
| | | | 600/14 |
| 2013/0035566 | A1 | 2/2013 | Mitragotri et al. |
| 2013/0338545 | A1 | 12/2013 | Azhari et al. |
| 2015/0045723 | A1* | 2/2015 | Paithankar .............. A61P 17/10 |
| | | | 604/22 |
| 2015/0174388 | A1 | 6/2015 | Slayton |
| 2015/0196229 | A1 | 7/2015 | Old et al. |
| 2017/0036002 | A1* | 2/2017 | Ignon ................... A61N 5/0617 |
| 2017/0329933 | A1 | 11/2017 | Brust et al. |
| 2018/0326208 | A1* | 11/2018 | Ingman ................... A61N 1/325 |
| 2019/0282450 | A1 | 9/2019 | Lam |
| 2020/0397611 | A1 | 12/2020 | Simmons et al. |
| 2021/0390418 | A1 | 12/2021 | Mass et al. |
| 2022/0167857 | A1 | 6/2022 | Lin |
| 2022/0384027 | A1 | 12/2022 | Kaleal, III et al. |
| 2023/0405319 | A1 | 12/2023 | Simon et al. |
| 2024/0180837 | A1 | 6/2024 | Seiner |
| 2024/0296348 | A1 | 9/2024 | Neumann |
| 2024/0361827 | A1 | 10/2024 | McNulty et al. |
| 2024/0420846 | A1 | 12/2024 | Hernandez et al. |
| 2025/0065144 | A1 | 2/2025 | Ansari et al. |
| 2025/0201420 | A1 | 6/2025 | Morse et al. |
| 2025/0210206 | A1 | 6/2025 | Ptaszek et al. |
| 2025/0242167 | A1 | 7/2025 | Opitz et al. |

FOREIGN PATENT DOCUMENTS

| | | |
|---|---|---|
| CN | 117726728 A | 3/2024 |
| WO | 2025054601 A1 | 3/2025 |

OTHER PUBLICATIONS

Micah J. Sheller, et al., Federated learning in medicine: facilitating multi-institutional collaborations without sharing patient data, Scientific Reports, 10, Article No. 12598, Jul. 28, 2020, 12 pages, Open access <https://doi.org/10.1038/s41598-020-69250-1>.

Ran Zhang, et al., EEG-based real-time BCI system using drones for attention visualization, Computer Methods in Biomechanics and Biomedical Engineering, Feb. 13, 2025, 11 pages, Taylor & Francis Online <https://doi.org/10.1080/10255842.2025.2459272>.

Office Action from U.S. Patent and Trademark Office, dated May 4, 2026, filed under U.S. Appl. No. 19/454,679, 33 pages.

\* cited by examiner

ACOUSTIC ISOLATION SYSTEM

TRANSPARENT COVER

PEMF COILS

CONTACT SENSOR

660nm and 850nm LEDs

DUAL-ZONE HEATING SYSTEM VENTS

ANTIMICROBIAL SURFACE

ULTRASONIC TRANSDUCER

CONTOURED

SMALL DISPLAY

CONTROL BUTTONS

HANDHELD ELECTROMAGNETTIC ENHANCEMENT DEVICE

Connected

Scan Barcode

Personalized Settings with AI

Session Progress

Upload & Compare Photos

Usage Analytics with Charts

Cloud Sync: Online ›

1

HANDHELD QUAD-MODAL SCALP TREATMENT DEVICE FOR ENHANCED HAIR LOSS THERAPEUTICS

BACKGROUND OF THE INVENTION

Hair loss has become an increasingly prevalent concern, driving continuous advancements in treatment modalities aimed at both efficacy and convenience. Conventional methods have ranged from topical solutions and oral medications to more invasive procedures, yet many still fall short in offering personalized, non-disruptive care. In recent years, research and development have focused on integrating multiple therapeutic approaches to address the multifaceted nature of scalp health, recognizing that effective treatment often requires a balance between stimulation, nourishment, and protection of hair follicles. This evolving landscape has underscored the importance of designing compact, user-friendly platforms that can adapt to individual treatment needs while ensuring consistent, optimal performance.

SUMMARY OF THE INVENTION

In one aspect, a handheld device for enhancing the topical absorption and efficacy of hair loss treatment compounds with integrated scalp analysis capabilities with a synchronized pulsed electromagnetic field (PEMF) generator; a dual-wavelength LED array; a zoned heating element; an ultrasonic molecular activation system operating at 20-35 kHz, a camera system with calibration targets; an adaptive protocol engine configured to receive real-time data from said integrated camera system, and in response, synchronously adjust at least one parameter of said PEMF generator, LED array, heating element, and ultrasonic system to optimize the delivery and efficacy of said hair loss treatment compounds; and a safety and control system including real-time scalp monitoring, follicular protection mechanisms, and acoustic exposure monitoring.

In another aspect, a handheld device is provided to enhance the topical absorption and efficacy of hair loss treatment compounds while offering integrated scalp analysis capabilities. In one aspect, the device comprises a scalp-contoured treatment head that delivers a four-mode enhancement system, which includes a synchronized pulsed electromagnetic field generator, a dual-wavelength light emitting diode array, a zoned heating element, an ultrasonic molecular activation system operating at a frequency of 20-35 kilohertz, and an integrated high-resolution camera system with calibration targets. In one aspect, an adaptive protocol engine is included that receives real-time data from the integrated camera system and synchronously adjusts one or more parameters of the pulsed electromagnetic field generator, light emitting diode array, heating element, and ultrasonic system to optimize the delivery and efficacy of the hair loss treatment compounds. In one aspect, a preset-based protocol engine is provided that selects optimal treatment parameters based on the classification of hair loss treatment compounds, including minoxidil, exosomes, finasteride, and platelet-rich plasma platelets. In one aspect, a modular safety and control system is provided that incorporates real-time scalp monitoring, follicular protection mechanisms, and acoustic exposure monitoring. In one aspect, a hybrid intelligence system is incorporated to provide onboard scalp safety control alongside application-based hair loss treatment optimization.

Advantages of one implementation may include one or more of the following. The disclosed device achieves an effect greater than the sum of its individual modalities through synchronized, sequential, and overlapping application. Specifically, ultrasonic cavitation at 20-35 kHz disaggregates treatment molecules and transiently increases scalp permeability by creating microchannels at the follicular level. This priming effect allows subsequent pulsed electromagnetic fields (PEMF) to more efficiently transport and activate those molecules, leveraging improved tissue conductivity and circulation. Concurrently, zoned heating reduces sebaceous barrier resistance and further facilitates compound diffusion into deeper scalp layers, while dual-wavelength photobiomodulation (660 nm red and 850 nm near-infrared) enhances mitochondrial ATP production, thereby increasing the cellular uptake and responsiveness to the delivered compounds. The interplay and interaction of these four synchronized distinct modalities establishes a dynamic cascade in which ultrasound enables PEMF efficiency, PEMF enhances thermal and circulatory effects, heating accelerates compound diffusion, and photobiomodulation drives intracellular assimilation. This integrated mechanism produces a synergistic therapeutic response not attainable with any subset of modalities alone.

Other advantages may include one or more of the following:

1. Enhanced Topical Absorption: The integration of a synchronized pulsed electromagnetic field generator, dual-wavelength LED array, zoned heating element, and ultrasonic molecular activation system works synergistically to improve the penetration and absorption of hair loss treatment compounds, potentially increasing their efficacy.

2. Personalized Treatment Delivery: By incorporating an adaptive protocol engine that receives real-time data from an integrated high-resolution camera system with calibration targets, the device can dynamically adjust treatment parameters. This allows the system to tailor therapy based on individual scalp health and compound characteristics, offering a personalized approach compared to one-size-fits-all treatments.

3. Comprehensive Multi-Modal Approach: The device's four-mode enhancement system combines electrical, optical, thermal, and ultrasonic energy modalities to provide complementary benefits. This multimodal approach addresses several aspects of scalp health—such as stimulation, nourishment, and protection of hair follicles—in a single, compact, and user-friendly platform.

4. Integration with Compound-Specific Protocols: The preset-based protocol engine enables the selection of optimized treatment parameters for a range of hair loss compounds (e.g., minoxidil, exosomes, finasteride, and platelet-rich plasma). This capability ensures that the device operates within the ideal therapeutic window for each agent, potentially augmenting their effectiveness while minimizing adverse effects.

5. Real-Time Safety and Control Features: The modular safety and control system constantly monitors scalp conditions via the integrated high-resolution camera and includes follicular protection mechanisms and acoustic exposure monitoring. This continuous feedback loop enhances patient safety during treatment by preventing overexposure to any one modality or energy source.

6. User Convenience and Portability: The handheld nature and scalp-contoured design of the device facilitate at-home use or clinical administration with minimal disruption to the user's routine. Its ease of use and compact design make it an attractive option for patients seeking non-invasive, customizable hair loss treatments that can be administered in a controlled and supervised manner.

7. Hybrid Intelligence for Onboard and App-Based Control: The incorporation of a hybrid intelligence system supports both onboard scalp safety control and application-based treatment optimization. This dual approach allows for seamless integration with external devices or monitoring systems, potentially enhancing the overall user experience and treatment outcomes.

Collectively, these advantages address the current limitations of conventional hair loss treatments by providing an integrated, adaptive, and multi-functional platform that optimizes the delivery, safety, and efficacy of topical hair loss treatment compounds.

DETAILED DESCRIPTION OF THE INVENTION

Figure 1:
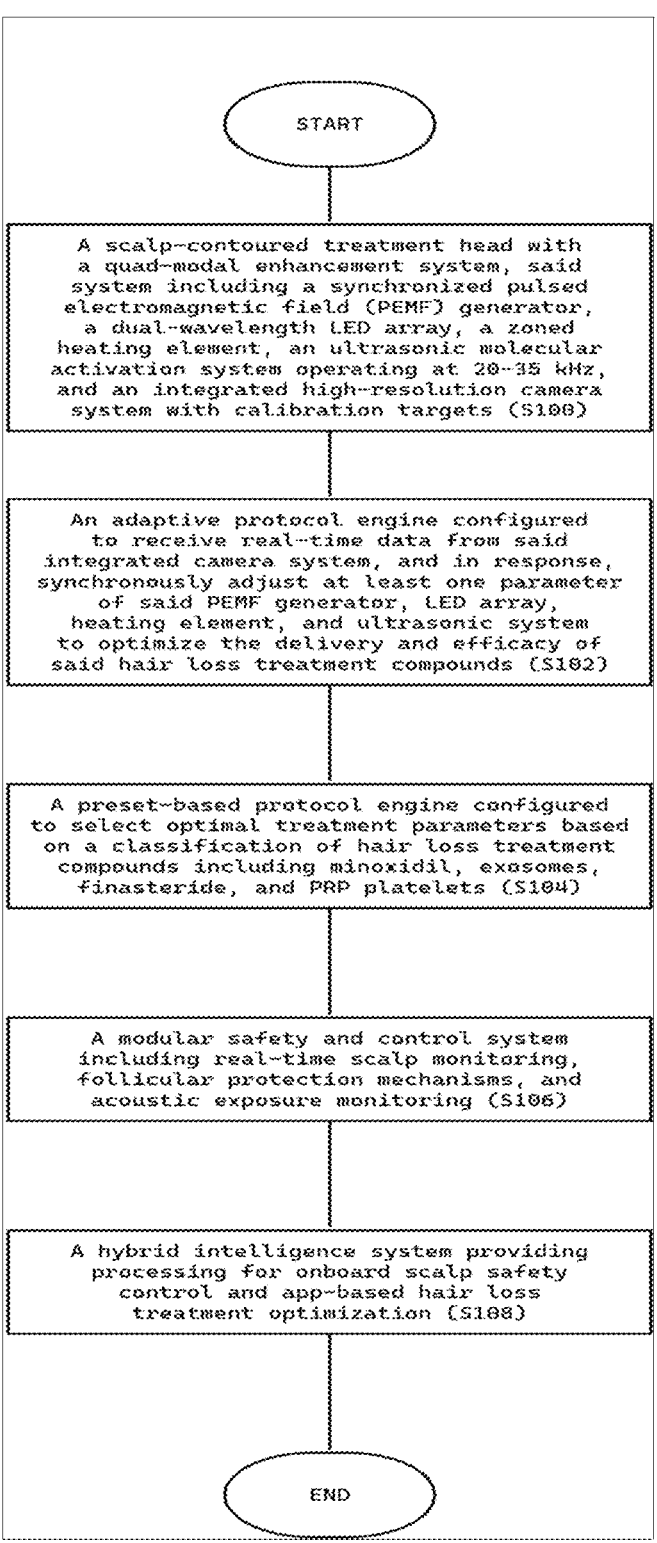
FIG. 1 illustrates a flowchart of a handheld quad-modal scalp treatment device process.

For purposes of this specification, the following terms are defined as follows:

PEMF (Pulsed Electromagnetic Field): Synchronized pulsed electromagnetic fields applied at continuous intervals to enhance molecular transport, improve scalp circulation, and stimulate follicular activity.

Ultrasonic Follicular Activation: The use of controlled acoustic cavitation (20-35 kHz) specifically calibrated for scalp tissue to disaggregate hair loss treatment molecules, create transient follicular microchannels, and enhance compound penetration to hair follicle stem cells and dermal papilla without damage to follicular structures.

Quad-Modal Follicular Enhancement: The synchronized application of electromagnetic, optical, thermal, and ultrasonic energies specifically optimized for hair follicle regeneration and compound delivery to scalp tissue.

Scalp Analysis System: Integrated camera and computer vision technology for quantitative assessment of hair density and thickness using calibrated measurement protocols.

Hair Density Measurement: Automated counting of hair follicles per square centimeter using computer vision algorithms and calibration targets.

Hair Thickness Analysis: Quantitative measurement of individual hair shaft diameter using optical analysis and perspective correction.

Progress Tracking: Longitudinal monitoring of hair density and thickness changes over treatment periods for efficacy assessment.

PBM (Photobiomodulation): The use of specific wavelengths of light (660 nm red, 850 nm near-infrared) to stimulate cellular processes, enhance ATP production in follicular cells, and improve compound absorption through scalp tissue.

Zoned Heating: A thermal control system utilizing multiple temperature zones optimized for scalp treatment to enhance molecular penetration while maintaining follicular safety.

Minoxidil Enhancement: Optimization of vasodilator delivery through ultrasonic disaggregation and electromagnetic stimulation to improve blood flow to hair follicles and extend anagen phase duration.

Exosome Activation: Enhancement of extracellular vesicle penetration and cellular uptake through acoustic cavitation for regenerative signaling in dormant follicles.

Finasteride Optimization: Improved delivery of $5\alpha$-reductase inhibitor through ultrasonic molecular disaggregation for localized DHT reduction without systemic exposure.

PRP Platelet Activation: Enhancement of growth factor release and cellular uptake from platelet-rich plasma through synchronized electromagnetic and ultrasonic stimulation for follicular regeneration.

Scalp-Specific Protocols: Treatment parameters optimized for scalp tissue characteristics including sebaceous activity, follicular density, dermal thickness, and acoustic properties.

Follicular Penetration: Enhanced delivery of therapeutic compounds to hair follicle stem cells and dermal papilla through multi-modal molecular disaggregation and transport enhancement.

One implementation describes a handheld device that incorporates a scalp-contoured treatment head designed to conform to the natural curvature of the scalp and maximize treatment efficiency. The treatment head houses a quad-modal enhancement system composed of several integrated components. The device comprises a scalp-contoured treatment head that delivers a four-mode enhancement system, which includes a synchronized pulsed electromagnetic field generator, a dual-wavelength light emitting diode array, a zoned heating element, an ultrasonic molecular activation system operating at a frequency of 20-35 kilohertz, and an integrated high-resolution camera system with calibration targets.

A synchronized pulsed electromagnetic field (PEMF) generator is provided to facilitate enhanced follicular circulation and promote active transport of therapeutic compounds, operating across three optimized frequency bands (5-15 Hz for minoxidil/PRP, 25-35 Hz for exosomes, and 45-55 Hz for finasteride). In addition, a dual-wavelength diode array (comprising 16 high-power 660 nm and 12 high-power 850 nm LEDs) is included to promote photobiomodulation and stimulate cellular responses within the scalp. The treatment head further comprises a zoned heating element engineered to locally elevate skin temperature (40-42° C. center zone, 38-40° C. outer zone) and enhance sebaceous barrier permeability, thereby supporting effective absorption of treatment formulations. An ultrasonic molecular activation system, operating at frequencies from 20 to 35 kilohertz using six PZT-4 ceramic transducers in a hexagonal configuration, is also integrated to achieve molecular disaggregation of compounds and reduce particle size by 70-85%. The assembly includes an integrated precision camera system equipped with calibration targets and acoustic isolation to enable accurate monitoring and data acquisition during treatment sessions.

FIG. 1 illustrates a flowchart of a handheld quad-modal scalp treatment device process. An adaptive protocol engine S102 is configured to receive real-time data from the integrated resolution camera system and multiple sensors (temperature, contact, EMF, and acoustic). The engine processes the imaging and sensor data to generate control signals that synchronously adjust operating parameters of the pulsed electromagnetic field generator (including frequency band selection), the dual-wavelength LED array (intensity balance between 660 nm and 850 nm outputs), the zoned heating element (precise temperature regulation), and the ultrasonic molecular activation system (power and frequency modulation). This dynamic adjustment optimizes both the delivery and the efficacy of the hair loss treatment compounds. By continuously monitoring scalp conditions during treatment, the protocol engine enables precise modulation of the treatment modalities, providing alterations that account for variations in scalp topography and tissue characteristics. The resulting synchronization between imaging feedback and treatment parameters ensures a controlled and effective treatment process while maintaining scalp safety.

One implementation further comprises a preset-based protocol engine S104, which is configured to select optimal treatment parameters based on a predetermined classification of hair loss treatment compounds comprising minoxidil (55-second protocol with 5-15 Hz PEMF), exosomes (75-second protocol with 25-35 Hz PEMF), finasteride (95-second protocol with 45-55 Hz PEMF), and PRP platelets (120-second protocol with 5-15 Hz PEMF). The protocol engine is designed to assess the specific characteristics of these compounds through barcode scanning or manual selection and accordingly establish control settings that optimize their delivery and effectiveness during treatment. This configuration ensures that each compound's inherent properties are accommodated within the treatment protocol, thereby enhancing the overall efficacy of the hair loss treatment regimen.

The system comprises a modular control and monitoring unit that continuously tracks scalp conditions in real time through multiple sensor systems, ensuring that treatment is administered only when environmental and physiological parameters fall within established acceptable ranges S106. This unit incorporates dedicated sensors that capture data on scalp temperature (with 0.1° C. resolution and 43° C. safety cutoff), humidity, contact alignment, and other essential factors, enabling the system to adjust its operation dynamically. In addition, the module features follicular protection mechanisms that actively prevent overexposure of hair follicles during treatment through real-time cavitation monitoring and automatic power adjustment. These mechanisms operate by detecting local conditions indicative of potential tissue stress or overheating and can temporarily deactivate or modify treatment outputs to maintain the integrity of the follicles. Furthermore, the module integrates acoustic exposure monitoring to track sound levels produced during treatment, ensuring that the energy delivered remains within allowable auditory thresholds, and EMF monitoring to verify safe field strengths. The collective operation of these features within the modular control system not only enhances the overall reliability of the device but also optimizes treatment delivery by providing continuous feedback and automatic adjustments, thereby preserving the scalp throughout the treatment process while maintaining efficacy.

A hybrid intelligence system S108, is integrated into the device to enable combined processing for both onboard scalp protection control and app-based hair loss treatment optimization. The system processes real-time data acquired from various sensors and an advanced resolution imaging system, ensuring that scalp protection parameters are continuously monitored and that treatment protocols are dynamically adjusted. The hybrid intelligence system operates in two primary modes: one dedicated to immediate local control to guard the scalp based on sensor feedback (with sub-100 ms response times for critical safety functions) and another that communicates with an external application to refine treatment settings remotely through cloud connectivity. This dual-mode operation allows S108 to facilitate secure treatment delivery while providing enhanced user control through a connected app that offers features including barcode scanning for compound identification, treatment progress tracking with computer vision analysis of follicular density and hair thickness, and ultrasonic responsiveness profiling, thereby improving the overall effectiveness and reliability of the hair loss treatment regimen.

Figure 2:
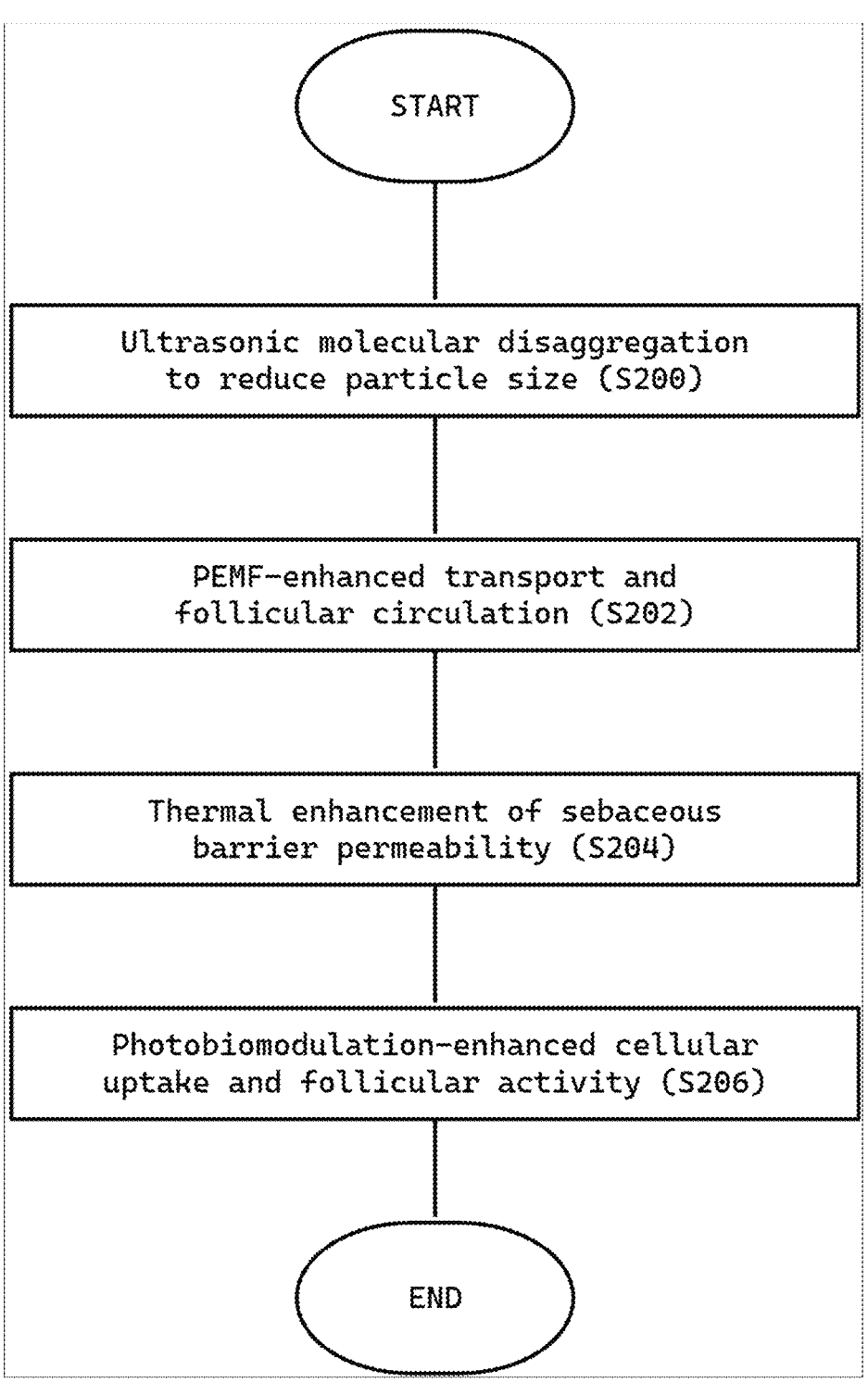
FIG. 2 illustrates a flowchart that shows a sequential flowchart depicting a multi-step hair loss treatment process.

FIG. 2 illustrates a flowchart outlining a multi-step process involving ultrasonic and photobiomodulation techniques. It begins with ultrasonic molecular disaggregation to reduce particle size S200, where six PZT-4 transducers operating at 22-30 kHz apply 25 W of focused acoustic energy for 10-15 seconds to create transient microchannels. This is followed by PEMF-enhanced transport and follicular circulation S202 using frequency-specific electromagnetic fields (5-55 Hz based on compound type). The next step involves thermal enhancement of sebaceous barrier permeability S204 through precisely controlled zoned heating (40-42° C. center, 38-40° C. periphery). Finally, photobiomodulation-enhanced cellular uptake and follicular activity S206 concludes the process through coordinated 660 nm/850 nm illumination with dynamically adjusted intensity based on real-time scalp reflectance measurements.

The ultrasonic molecular disaggregation method S200, is designed to reduce the particle size of compounds used in hair loss treatments by 70-85%. Utilizing ultrasonic waves at frequencies between 20 and 35 kilohertz from six piezoelectric transducers arranged in a hexagonal configuration, the process stimulates molecular movement while maintaining follicular safety through real-time cavitation monitoring, thereby enhancing the absorption of the active ingredients into the scalp. This reduction in particle size helps to improve the delivery efficiency of the treatment compounds through created transient microchannels in the sebaceous barrier.

One implementation comprises a handheld device designed to augment the effectiveness of hair loss treatment compounds. A central element of the device is a PEMF-enhanced transport and follicular circulation system, designated as S202. This system employs pulsed electromagnetic fields in three optimized frequency ranges (5-15 Hz for minoxidil/PRP, 25-35 Hz for exosomes, 45-55 Hz for finasteride) to facilitate augmented transport of treatment compounds and circulation within the hair follicles, potentially resulting in increased absorption and efficacy of the treatments applied. The design aims to optimize the interaction between the treatment compounds and the scalp, thereby addressing hair loss with greater efficiency through frequency-specific stimulation protocols.

The reference label "thermal enhancement of sebaceous barrier permeability" S204 pertains to the process within the device where a zoned heating element comprising 32 independently controllable resistive elements is utilized to increase the permeability of the sebaceous barrier. This enhancement aids in the effective transport of hair loss treatment compounds into the scalp by facilitating the opening of pathways through precisely controlled heat application (40-42° C. center zone, 38-40° C. outer zone), with continuous infrared monitoring ensuring safe and effective temperature distribution. The targeted thermal application ensures optimal absorption of compounds, improving the treatment's efficacy by enabling deeper penetration at the follicular level while preventing tissue damage through automatic power regulation.

The photobiomodulation-enhanced cellular uptake and follicular activity (S206) employs specific wavelengths of electromagnetic energy (16×660 nm and 12×850 nm LEDs with optical collimators) to stimulate cellular processes and boost the activity within hair follicles. This method is designed to improve the absorption of compounds used in hair loss treatments through pulsed operation (50-100 Hz) with dynamically adjusted duty cycles, thereby increasing their effectiveness. By promoting enhanced cellular activity through mitochondrial stimulation and increased ATP production, the process optimizes follicular responsiveness to the treatment, supporting hair regrowth and overall scalp health while incorporating active cooling mechanisms to maintain safe operating temperatures.

Figure 3:
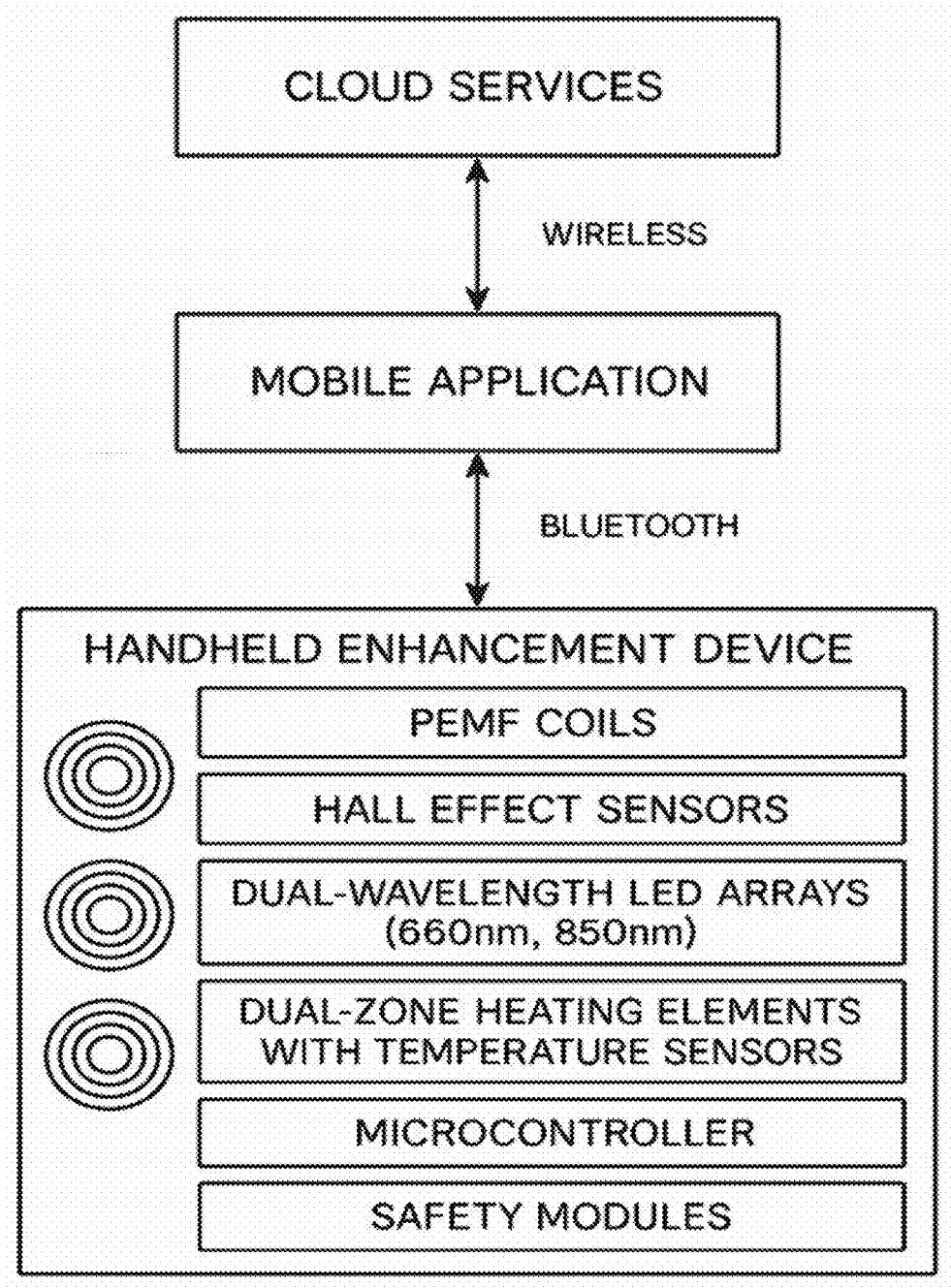
FIG. 3 shows the architecture of a handheld enhancement platform.

FIG. 3 illustrates a three-tier hierarchical architecture of the hair loss treatment platform, representing a comprehensive ecosystem designed to optimize therapeutic outcomes through intelligent coordination. At the top level, Cloud Services forms the computational backbone that houses extensive databases containing compound profiles for different hair loss treatments including minoxidil, finasteride, exosomes, and PRP, along with treatment protocols and anonymized session analytics collected from users worldwide. This cloud layer enables continuous AI optimization of therapeutic algorithms through machine learning analysis of treatment outcomes, while also providing remote firmware updates to ensure devices operate with the latest safety protocols and efficacy improvements. The middle tier represents the Mobile Application, which serves as the bidirectional interface between cloud intelligence and the physical device, facilitating user interaction through treatment customization, real-time session monitoring of the quad-modal enhancement process, and barcode scanning capabilities for automatic compound identification, while simultaneously relaying treatment data to the cloud for continuous AI refinement and protocol optimization.

At the foundation lies the Handheld Enhancement Device, depicted with six clearly labeled subsystems that implement the revolutionary quad-modal therapeutic approach for hair loss treatment. The PEMF coils generate tissue-specific electromagnetic pulses at frequencies precisely optimized for different hair loss compounds, operating at 5-15 Hz for minoxidil and PRP treatments to enhance vasodilation and platelet activation, 25-35 Hz for exosome therapy to increase membrane permeability for regenerative signaling, and 45-55 Hz for finasteride delivery to optimize sebaceous barrier penetration for localized DHT reduction. Adjacent blocks showcase the dual-wavelength LED arrays operating at 660 nm and 850 nm wavelengths for photobiomodulation therapy, while dual-zone heating elements with embedded thermistors provide controlled thermal enhancement to improve sebaceous barrier permeability and compound absorption. A centralized microcontroller orchestrates the precise synchronization of all modalities and continuously performs safety checks, while dedicated safety modules enforce real-time monitoring of electrical, thermal, and acoustic thresholds through hardware interlocks that can respond within sub-100 ms timeframes to prevent any potential follicular damage.

Figure 4:
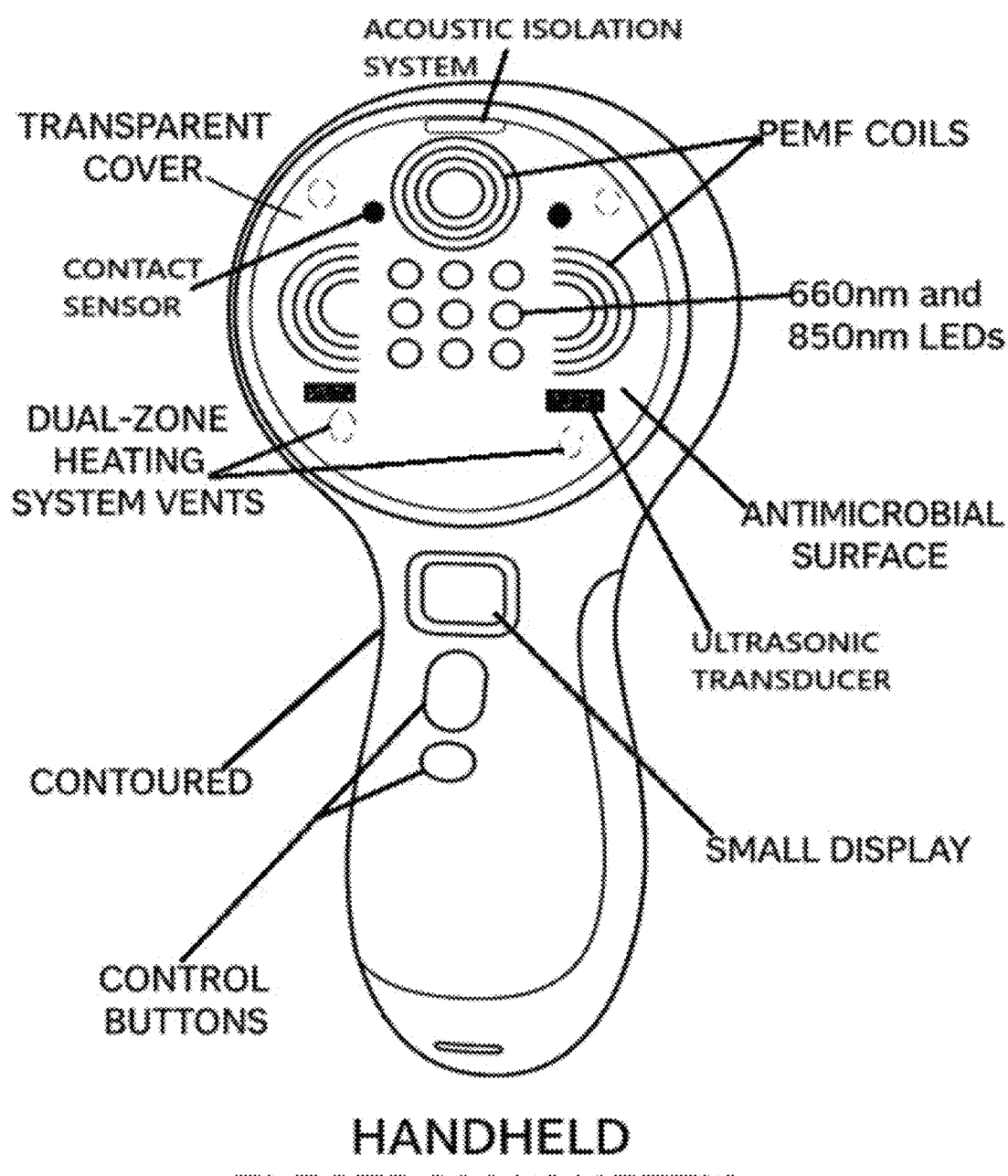
FIG. 4 shows a handheld electromagnetic enhancement device

FIG. 4 shows a detailed cross-sectional view of the handheld hair treatment device, showcasing how multiple therapeutic modalities are seamlessly combined in an ergonomic form factor specifically designed for scalp treatment applications. The scalp-contoured treatment head represents a design innovation, engineered to conform precisely to the natural curvature of the human scalp and provide optimal contact across the designated 35-45 cm$^2$ treatment area, ensuring uniform energy distribution and maximum therapeutic efficacy during hair loss treatment sessions. At the top of the device head, the acoustic isolation system serves a dual purpose of insulating ultrasonic emissions to minimize disruptive noise while enhancing the precision and efficiency of ultrasonic energy delivered to scalp tissue, protected by a transparent cover that safeguards internal components while maintaining visibility of indicator lights and device contact status without interfering with the complex therapeutic functions occurring beneath.

The PEMF coils are strategically positioned to generate the pulsed electromagnetic fields that stimulate cellular activity, promote tissue regeneration, and significantly boost the absorption of topical hair loss formulations through frequency-specific stimulation protocols. Adjacent to these coils, the contact sensor ensures proper device positioning on the scalp before activating any therapy, thereby enhancing both safety and treatment accuracy by preventing accidental activation when the device is not properly positioned. The central area houses clusters of precisely arranged 660 nm red and 850 nm near-infrared LEDs that deliver photobiomodulation therapy, effectively enhancing cellular repair processes and increasing ATP production in follicular cells by 30-50%, while improving blood perfusion by 40-60% to promote hair growth and overall scalp health. The ultrasonic transducers, embedded within the treatment head as six PZT-4 ceramic elements arranged in a hexagonal configuration, emit high-frequency sound waves at 20-35 kHz that mechanically stimulate molecular movement and create controlled acoustic cavitation, facilitating the disaggregation of hair loss treatment molecules and reducing particle size by 70-85% while creating transient microchannels for dramatically enhanced penetration and absorption of therapeutic compounds.

Surrounding the treatment head, dual-zone heating system vents enable adaptive thermal control by generating precisely controlled heat in multiple focused zones, with the center zone maintained at 40-42° C. and the outer zone at 38-40° C., optimizing drug delivery efficacy and patient comfort by tailoring thermal application to enhance sebaceous barrier permeability for improved compound absorption. The treatment surface incorporates an antimicrobial coating that reduces bacterial colonization and infection risk during repeated use, ensuring hygienic operation throughout extended treatment protocols. The ergonomically contoured handle offers a comfortable and secure grip that ensures precise maneuverability across various scalp regions, while the small display provides real-time feedback on device status, active treatment modes, session timers, and battery life, enabling users to maintain awareness and control over the treatment process. Conveniently positioned control buttons allow users to power the device on or off, toggle between different treatment modes optimized for specific hair loss compounds, adjust heating levels or power output based on individual comfort and response, and start or stop treatment sessions with precision timing for compound-specific protocols.

Figure 5:
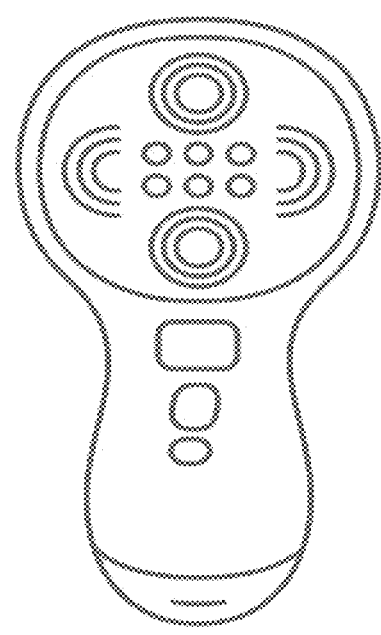
FIG. 5 shows a mobile application interface.
Figure 5:
Figure 5:
Figure 5:
Figure 5:
Figure 5:
Figure 5:

FIG. 5 shows a mobile application interface representing the software ecosystem that transforms the handheld device into an intelligent, personalized hair loss treatment system through seamless integration of AI-driven optimization and real-time monitoring capabilities. The Bluetooth "Connected" status at the top indicates active wireless communication between the handheld device and mobile application, which is essential for real-time data transmission, parameter adjustment, and continuous monitoring during hair loss treatment sessions, enabling the hybrid intelligence system to provide both immediate onboard safety control and cloud-based treatment optimization. The central element displays a detailed schematic representation of the handheld device itself, illustrating its ergonomic form factor with the rounded treatment head prominently featured at the top, showing the spatial arrangement of the dual-wavelength LED arrays represented by large circular elements operating in the red and near-infrared spectrum, while a central cluster of six smaller circles depicts the ultrasonic transducer array operating at frequencies between 20-35 kHz for molecular disaggregation and enhanced compound delivery.

The "Scan Barcode" feature enables automatic identification of topical hair loss treatment compounds including minoxidil, finasteride, exosomes, and PRP, triggering the AI system to instantly select optimal treatment protocols based on each compound's unique molecular characteristics, pharmacokinetic properties, and required enhancement parameters. The "Personalized Settings with AI" functionality employs the AI-driven protocol engine to customize treatment parameters based on individual user scalp profiles derived from computer vision analysis, real-time dermal assessment data, and historical response patterns, ensuring that electromagnetic frequencies, LED intensities, heating profiles, and ultrasonic settings are precisely tailored for maximum follicular enhancement and compound bioavailability.

The "Session Progress" indicator provides comprehensive real-time feedback on treatment status, displaying remaining time for compound-specific duration protocols, current modality intensity levels during the synchronized quadmodal enhancement process, and safety parameter status to ensure optimal treatment delivery while maintaining follicular protection. The "Upload & Compare Photos" feature supports the integrated computer vision system by capturing and analyzing before-and-after treatment photographs to quantitatively measure changes in hair density (follicles per square centimeter), hair shaft thickness, and overall scalp condition, providing objective assessment of treatment efficacy over time and enabling protocol adjustments based on measurable outcomes. The "Usage Analytics with Charts" functionality delivers comprehensive treatment data analysis through cloud-based processing, tracking detailed treatment history, compound-specific response patterns, and long-term efficacy metrics to continuously optimize future hair loss treatment protocols based on individual bioavailability patterns and follicular responsiveness.

The "Cloud Sync: Online" status with directional arrow confirms that the device maintains continuous connection with the cloud-based AI processing system, enabling the advanced analytics, real-time protocol updates, and hybrid intelligence architecture that distinguishes this hair loss treatment system from conventional topical application methods. The bottom navigation bar contains six strategically designed icons representing different application sections including the home dashboard for treatment overview, settings and controls for parameter customization, comprehensive treatment history tracking, AI-driven protocol library containing optimized settings for various hair loss compounds, long-term progress tracking with computer vision analysis of follicular improvements, and user support information for troubleshooting and guidance, collectively supporting the patent's key innovations in delivering personalized, intelligent, and measurably effective hair loss treatment through sophisticated technological integration. In one embodiment, a pulsed electromagnetic field (PEMF) generator is arranged to operate in multiple follicle-optimized frequency bands. For example, the PEMF generator is configured for a low frequency band with a range of approximately 5 to 15 Hz to enhance the effects of minoxidil delivery (through vasodilation) and to activate PRP platelets near the scalp follicles (through improved degranulation). In another configuration, the PEMF generator operates in a mid-frequency band with a range of approximately 25 to 35 Hz that is selectively applied for optimizing exosome activation (by increasing membrane permeability). In a further configuration, the PEMF generator operates in a high frequency band with a range of approximately 45 to 55 Hz to facilitate the delivery optimization of finasteride to the hair follicles (through enhanced sebaceous barrier penetration). The selection and control of these frequency bands is dynamically adjusted by an adaptive protocol engine that receives real-time data from an integrated camera system and other sensors. The adaptive protocol engine synchronously modifies the operating parameters of the PEMF generator based on treatment conditions and real-time monitoring, thereby ensuring that the selected frequency band is applied according to the classification of the hair loss treatment compound being utilized. This configuration permits targeted electromagnetic stimulation that enhances the therapeutic effects of each compound while maintaining optimal treatment conditions at the scalp level.

Applying the reduced-frequency PEMF is precisely coordinated with ultrasonic molecular disaggregation, a process that diminishes the particle size of treatment compounds by 70-85% to facilitate superior absorption and tissue penetration. The concurrent action of ultrasonic disaggregation (using six PZT-4 transducers at 20-35 kHz) and the reduced-frequency PEMF results in more effective permeation of minoxidil and PRP constituents through the skin's sebaceous barrier, enhancing both the cellular uptake of the active agents and their bioavailability at the follicular level. The resulting effect is a dual therapeutic benefit derived from the augmented vasodilation exhibited by minoxidil and the robust release of growth factors from PRP platelets, with the entire process being continuously monitored and adjusted through real-time sensor feedback to maintain safety and efficacy.

In one embodiment, the dual-wavelength LED array includes sixteen powerful 660 nm emitting diodes (150 mW each) arranged to target and activate follicular cells through photobiomodulation, each diode producing sufficient irradiance to stimulate cellular metabolic pathways associated with hair growth. The 660 nm wavelength is selected for its capacity to interact with cytochrome c oxidase in mitochondria, thereby enhancing adenosine triphosphate production by 30-50% and promoting follicular regeneration. In addition, the array incorporates twelve powerful 850 nm emitting diodes (200 mW each) designed to provide deeper penetration (4-6 mm) into scalp tissue for stimulation of the dermal papilla; this wavelength has been demonstrated to facilitate improvements in blood perfusion by 40-60% and promote cellular proliferation in the deeper layers of skin tissue. The diode elements are positioned in a spatial configuration that ensures optimal energy distribution, guaranteeing that both superficial and deep tissue effects are achieved uniformly. The powerful 850 nm diodes are arranged in coordinated alignment with ultrasonic transducers such that the optical emission is complemented by ultrasonic energy operating at frequencies between 20 and 35 kHz. This arrangement permits simultaneous ultrasonic activation, wherein ultrasonic energy disrupts molecular aggregations and enhances tissue permeability, thereby facilitating deeper penetration of the emitted optical radiation and any concurrently applied therapeutic compounds. The spatial relationship between the diode array and the ultrasonic transducers is engineered to maximize synchronicity between photonic and ultrasonic treatments, ensuring that the benefits of cellular activation and deep tissue stimulation are realized concurrently. Moreover, the diode array is configured with optical collimators (30° beam angle) and reflective elements that aid in directing and focusing the emitted radiation, and with supplemental heat dissipation features (maintaining junction temperatures below 60° C.) to manage thermal output during extended use. In selected embodiments, control circuitry is incorporated to dynamically adjust diode intensity and pulsing patterns (50-100 Hz) in synchronization with ultrasonic transducer operation, allowing for real-time modulation of treatment parameters in response to feedback from integrated monitoring systems.

In one embodiment, the zoned heating element is configured to maintain a center zone temperature between 40° C. and 42° C. while regulating an outer zone temperature between 38° C. and 40° C., with all temperatures continuously monitored by high-resolution infrared sensors. The heating element includes 32 discrete thermal control regions that enable independent temperature management across the treatment head, with each resistive element being individually addressable by the control system. The center zone, maintained at the higher temperature range, is optimized to create localized conditions that enhance the efficacy of the simultaneous ultrasonic molecular activation process, whereas the outer zone is kept slightly cooler to ensure patient safety and minimize potential thermal stress on surrounding scalp tissues. To achieve these temperature setpoints, the heating element incorporates a combination of resistive heating elements and thermal sensors that continuously monitor real-time temperature feedback at 10 Hz update rates. The sensor outputs are fed into the adaptive protocol engine, which dynamically adjusts power delivery to the resistive elements to counteract potential heat loss or excess heat generation, especially that which can occur from the ultrasonic subsystem's operation. In this configuration, thermal management is further refined by balancing the heat generated ultrasonically with the controlled resistive heating; this synergy mitigates the risk of localized overheating while promoting the desired molecular activation effects. The integration of such a zoned heating element not only improves the controlled delivery of thermal energy but also ensures that the heating profile is maintained within narrowly defined parameters, thereby optimizing the overall treatment process and enhancing the stability and effectiveness of the associated hair loss treatment compounds through precise temperature regulation.

In one embodiment, the device is configured to implement a scalp-optimized quad-modal power ramping profile that delivers energy in a sequential, controlled manner to achieve optimal hair loss treatment while preserving scalp integrity. The profile first initiates an ultrasonic follicular priming phase operating at 25W. During this phase, the ultrasonic molecular activation system delivers targeted ultrasonic energy to the scalp at 22-30 kHz for 10-15 seconds, thereby inducing molecular disaggregation and reducing particle size by 70-85%. The priming phase prepares hair follicles for subsequent treatment steps by facilitating the initial permeabilization of the follicular structure and enhancing readiness for compound uptake through created transient microchannels.

Following this, the device transitions into a peak follicular enhancement phase during which a higher power level of 50 W is applied through coordinated operation of all four modalities. This increased energy output is designed to maximize stimulation of hair follicles, facilitating enhanced transport and circulation within the follicular environment, and it works in concert with other treatment modalities, such as pulsed electromagnetic field enhancement (at compound-specific frequencies) and photobiomodulation (with wavelength-balanced output), to boost cellular activity and promote hair regrowth. The system then enters a sustained follicular stimulation phase at 45W to maintain therapeutic effects while conserving energy.

In one embodiment, the ultrasonic molecular activation system comprises six piezoelectric transducers that are arranged in a hexagonal configuration, thereby ensuring an even distribution of ultrasonic energy across the treatment head. The transducers are engineered to operate within a frequency range of 20 to 35 kilohertz, which is selected to optimize the generation of ultrasonic waves that promote molecular disaggregation of hair loss therapeutics while maintaining follicular safety. The overall system is designed to deliver a combined power output between 8 and 18 watts (1-3 W per transducer), ensuring sufficient energy to achieve effective particle size reduction while maintaining safety thresholds. Additionally, the system incorporates real-time cavitation monitoring that continuously assesses the ultrasonic energy being applied through impedance measurements, thus enabling dynamic modulation to prevent excessive cavitation which could lead to follicular damage. This monitoring mechanism facilitates a feedback loop that automatically adjusts the operational parameters (including frequency, power, and duty cycle), ensuring that the molecular disaggregation process is maximized for therapeutic efficacy without compromising the integrity of the scalp tissue.

The six piezoelectric transducers are fabricated from a PZT-4 ceramic composition recognized for its exemplary piezoelectric coefficients and extended operational stability, ensuring reliable ultrasonic energy generation when energized. Each transducer is coupled with a titanium backing plate that not only provides robust mechanical support but also improves acoustic impedance matching between the ceramic material and the scalp tissue, thereby optimizing energy transfer. The titanium backing plates are engineered to enhance scalp coupling efficiency while minimizing unwanted vibrational resonances that could detract from treatment efficacy. These transducers are strategically positioned between LED clusters that form part of the device's dual-wavelength LED array, which facilitates simultaneous photobiomodulation. To ensure that the acoustic energy emitted by the piezoelectric elements is effectively directed toward the target scalp regions without interfering with the adjacent LED clusters, specialized follicular-compatible acoustic isolation materials (fluoropolymer barriers providing 42 dB vibration reduction) are interposed between the transducers and the LED clusters. These acoustic isolation materials are selected for their biocompatibility and their ability to attenuate mechanical vibrations that might otherwise disrupt the delicate balance of energy distribution across the treatment head. By acoustically isolating the transducers, the design ensures that ultrasonic energy is focused for optimal molecular activation of the treatment compounds and for enhancing follicular uptake, while also protecting the integrity and function of the LED clusters. This arrangement not only maximizes the therapeutic benefits of both the ultrasonic and photobiomodulation modalities but also promotes patient well-being and comfort during hair loss treatment applications.

Alongside temperature monitoring, the system integrates contact sensors positioned on the treatment head to verify that the device maintains consistent contact with the scalp across the entire 35-45 cm$^2$ treatment area. Such sensors ensure proper alignment and positioning, thereby optimizing treatment efficacy while reducing the chance of unintended exposure beyond the target treatment area. Additionally, electromagnetic field monitors are incorporated to measure the levels of electromagnetic radiation within the treatment zone. These monitors compare detected electromagnetic field strengths with established exposure limits (maintaining 2-5 mT at the scalp surface), ensuring that any deviation from permitted operating conditions is promptly identified and corrected through automatic power adjustment.

Complementing these features is an acoustic monitoring component that continuously evaluates the ultrasonic energy emitted by the molecular activation system through real-time impedance measurements. This element works in conjunction with an automatic ultrasonic power limitation feature that actively adjusts the ultrasonic generator's output when acoustic energy levels surpass predetermined thresholds for safe cavitation. Each component of the enhanced scalp protection monitoring system operates in an integrated manner, enabling real-time adjustments to be communicated to the treatment head's control algorithms at sub-100 ms response times. This integration ensures that any potentially hazardous operational conditions are quickly addressed, keeping exposure levels within defined parameters while allowing therapeutic settings to remain optimally controlled for maximum treatment efficacy.

In an alternative embodiment, the hair loss treatment system incorporates a mobile application interface configured to identify hair loss treatment compounds through barcode scanning with ultrasonic responsiveness analysis and automatically select corresponding follicular enhancement protocols. In this embodiment, the mobile application interface is programmed to capture a digital image of a barcode associated with a given hair loss treatment compound and to analyze ultrasonic responsiveness data (derived from real-time impedance measurements), thereby discerning the chemical composition, concentration, and overall suitability of the compound for treatment use. Once the hair loss treatment compound is identified, the mobile application interface communicates the compound's information to the system's protocol engines. For instance, based on the compound identification, the interface directs a preset-based protocol engine to select a predetermined combination of treatment parameters (including specific PEMF frequencies, LED balances, heating profiles, and ultrasonic settings) or instructs an adaptive protocol engine to modify treatment parameters in real time according to the compound's characteristics. This automatic selection of corresponding follicular enhancement protocols enables the treatment system to optimize the delivery efficiency and biological activity of the compound, thereby ensuring that the treatment head—which includes a synchronized PEMF generator, dual-wavelength LED array, zoned heating element, and ultrasonic molecular activation system—applies parameters finely tuned to promote enhanced follicular uptake. The integration of the mobile application interface with ultrasonic responsiveness analysis further enhances the system's ability to dynamically customize treatment protocols, thus improving both efficacy and safety during administration of the hair loss treatment compounds through continuous performance optimization.

In one embodiment, the treatment head is designed to complement the natural curvature of the scalp, thereby ensuring intimate contact with the treatment site and providing a coverage area in the range of 35-45 cm$^2$. This strategically contoured design allows for comprehensive scalp treatment by ensuring that therapeutic agents are uniformly administered across a contiguous area. Furthermore, the treatment head supports the administration of compound-specific duration protocols (55 seconds for minoxidil, 75 seconds for exosomes, 95 seconds for finasteride, and 120 seconds for PRP), wherein the treatment duration is tailored to the pharmacokinetic and pharmacodynamic properties of the specific hair loss compounds being delivered. By accommodating variable treatment times and automatically adjusting power profiles (25 W priming, 50 W peak, 45 W sustained), the device optimizes the absorption and effectiveness of the compounds used while maintaining strict safety parameters throughout each session.

Additionally, the treatment head incorporates an acoustic isolation feature essential for preventing cross-modality interference among the various therapeutic systems integrated within the device. For example, the isolation mechanism includes specialized fluoropolymer materials and structural elements designed to dampen and segregate operational noise and vibrations (achieving 42 dB reduction) generated by the ultrasonic molecular activation system from other modalities, such as the synchronized pulsed electromagnetic field generator and dual-wavelength LED array. Through this acoustic isolation, each modality performs at its designed parameters without the disruptive influence of adjacent systems, thereby ensuring reliable and effective treatment delivery. The isolation system is particularly critical during simultaneous ultrasonic and photobiomodulation treatment phases, where vibrational energy from the transducers could otherwise interfere with precise optical delivery if not properly contained.

Localized ultrasonic enhancement not only aids in particle disaggregation (achieving 70-85% size reduction) but also improves compound delivery efficiency by temporarily increasing scalp tissue permeability and fostering primarily localized circulation along the hair follicles through created microchannels. The PEMF-enhanced transport feature further directs the movement of compounds toward the desired target areas using frequency-specific electromagnetic fields (5-15 Hz for minoxidil/PRP, 25-35 Hz for exosomes, 45-55 Hz for finasteride), while the combination of thermal effects (40-42° C. center zone) and optical modulation (660 nm/850 nm balanced output) facilitates optimal cellular uptake without triggering elevated systemic concentrations. Additionally, the modular risk management and control system provides real-time scalp monitoring (temperature, contact, EMF, acoustic), follicular protection mechanisms (including cavitation monitoring and automatic power adjustment), and acoustic exposure surveillance to ensure that treatment parameters remain within controlled operational limits during each session, with all safety systems operating at sub-100 ms response times for maximum protection.

In one embodiment, the integrated camera system is mounted within the scalp-contoured treatment head and is acoustically isolated from the ultrasonic components through viscoelastic mounts to prevent interference from vibrational energy generated during operation of the ultrasonic molecular activation system. The camera system is configured with computer vision algorithms capable of analyzing images captured during treatment to track hair restoration progress through quantitative measurement of follicular density (follicles/cm$^2$) and hair shaft diameter (μm) using perspective correction and calibration reticles. These algorithms perform advanced image processing techniques that monitor changes in follicular density and scalp condition, thereby providing quantitative and qualitative analysis of ultrasonic treatment effectiveness on follicular health and the delivery of hair loss treatment compounds. The data generated are communicated in real time to adaptive control modules, allowing for dynamic adjustments to treatment parameters to optimize efficacy and safety based on observed progress. Longitudinal tracking through the mobile application enables users and professionals to assess treatment outcomes over time, with the system automatically refining protocols based on individual response patterns for personalized hair restoration therapy.

The invention claimed is:

1. A handheld device for enhancing the topical absorption and efficacy of hair loss treatment compounds with integrated scalp analysis capabilities comprising:

a synchronized pulsed electromagnetic field (PEMF) generator;

a dual-wavelength light emitting diode (LED) array;

a zoned heating element;

an ultrasonic molecular activation system operating at 20-35 kHz, and an camera system with calibration targets;

an adaptive protocol engine configured to receive real-time data from said integrated camera system, and in response, synchronously adjust at least one parameter of said PEMF generator, LED array, heating element, and ultrasonic system to optimize the delivery and efficacy of said hair loss treatment compounds; and a safety and control system including real-time scalp monitoring, follicular protection mechanisms, and acoustic exposure monitoring.

2. The device of claim 1, wherein the PEMF generator is configured to operate in follicle-optimized frequency bands, including a low frequency band (5-15 Hz) for minoxidil enhancement and platelet-rich plasma (PRP) platelet activation, a mid-frequency band (25-35 Hz) for exosome optimization, and a high frequency band (45-55 Hz) for finasteride delivery optimization.

3. The device of claim 2, wherein the low frequency PEMF (5-15 Hz) is configured to enhance minoxidil vasodilation effects and stimulate PRP platelet degranulation for improved growth factor release, coordinated with ultrasonic molecular disaggregation.

4. The device of claim 2, wherein the mid frequency PEMF (25-35 Hz) is configured to enhance exosome membrane permeability and cellular uptake for improved regenerative signaling to dormant hair follicles, synchronized with acoustic cavitation for enhanced delivery.

5. The device of claim 2, wherein the high frequency PEMF (45-55 Hz) is configured to optimize finasteride penetration through sebaceous barriers while maintaining localized follicular concentration, enhanced by ultrasonic molecular disaggregation.

6. The device of claim 1, wherein the dual-wavelength LED array is configured with 16 high-power 660 nm LEDs for follicular cellular activation and 12 high-power 850 nm LEDs for deep scalp penetration and dermal papilla stimulation, arranged in coordination with ultrasonic transducers.

7. The device of claim 1, wherein the zoned heating element is configured to maintain a center zone temperature between 40-42° C. and an outer zone temperature between 38-40° C., with thermal management optimized for ultrasonic heat generation.

8. The device of claim 1, wherein the adaptive protocol engine automatically adjusts treatment duration based on hair loss compound type and ultrasonic responsiveness.

9. The device of claim 1, wherein the device is configured to implement a scalp-optimized quad-modal power ramping profile including an ultrasonic follicular priming phase (25 W), a peak follicular enhancement phase (50 W), and a sustained follicular stimulation phase (45 W).

10. The device of claim 1, wherein the ultrasonic molecular activation system comprises six piezoelectric transducers arranged in hexagonal pattern and real-time cavitation monitoring to prevent follicular damage while maximizing molecular disaggregation effects in hair loss therapeutics.

11. The device of claim 10, wherein the ultrasonic system operates in a three-phase protocol comprising follicular priming at 22-30 kHz for 10-15 seconds, synchronized low-level enhancement during quad-modal treatment, and a follicular penetration boost for enhanced compound delivery and wherein the six piezoelectric transducers are positioned between LED clusters with specialized follicular-safe acoustic isolation materials.

12. The device of claim 1, wherein the integrated camera system includes acoustic isolation from ultrasonic components and computer vision algorithms for tracking hair restoration progress including analysis of ultrasonic treatment effectiveness on follicular health and compound delivery.

13. The device of claim 1, wherein the enhanced scalp safety monitoring system includes temperature sensors configured to prevent follicular overheating, contact sensors for proper scalp positioning, electromagnetic field monitors for safe exposure levels, and acoustic exposure monitoring with automatic ultrasonic power limitation.

14. The device of claim 1, further comprising a mobile application interface configured to identify hair loss treatment compounds through barcode scanning with ultrasonic responsiveness analysis and automatically select corresponding follicular enhancement protocols.

15. The device of claim 1, wherein the treatment head has a scalp-contoured configuration providing 35-45 cm$^2$ coverage area enabling comprehensive scalp treatment with compound-specific duration protocols and acoustic isolation preventing cross-modality interference and wherein the ultrasonic molecular activation system is configured to create controlled acoustic cavitation for hair loss compound disaggregation reducing particle size by 70-85% while maintaining follicular safety through real-time monitoring and automatic power adjustment.

16. The device of claim 1, comprising a treatment engine configured to select parameters based on a classification of hair loss treatment compounds including minoxidil, exosomes, finasteride, and PRP platelets.

17. The device of claim 1, further comprising scalp condition assessment capabilities configured to adjust quad-modal treatment parameters based on sebaceous activity, follicular density, hair loss severity, and acoustic properties of scalp tissue.

18. The device of claim 1, wherein the device is configured for daily hair loss treatment sessions with adaptive protocols that optimize therapeutic compound delivery while minimizing systemic absorption and side effects through localized ultrasonic enhancement.

* * * * *